US011793961B2

(12) United States Patent
Chun et al.

(10) Patent No.: US 11,793,961 B2
(45) Date of Patent: Oct. 24, 2023

(54) ESOPHAGEAL TEMPORARY OCCLUSION DEVICE AND METHOD FOR ENDOTRACHEAL INTUBATION AND OROGASTRIC TUBE INSERTION

(71) Applicants: University of Pittsburgh—Of the Commonwealth System of Higher Education; UPMC, Pittsburgh, PA (US)

(72) Inventors: Youngjae Chun, Pittsburgh, PA (US); Philip Charles Carullo, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 1129 days.

(21) Appl. No.: 16/341,123

(22) PCT Filed: Oct. 18, 2017

(86) PCT No.: PCT/US2017/057139
§ 371 (c)(1),
(2) Date: Apr. 11, 2019

(87) PCT Pub. No.: WO2018/075616
PCT Pub. Date: Apr. 26, 2018

(65) Prior Publication Data
US 2020/0179630 A1    Jun. 11, 2020

Related U.S. Application Data

(60) Provisional application No. 62/409,455, filed on Oct. 18, 2016.

(51) Int. Cl.
*A61M 16/04* (2006.01)
*A61B 17/12* (2006.01)
*A61M 25/00* (2006.01)

(52) U.S. Cl.
CPC .... *A61M 16/0409* (2014.02); *A61M 16/0463* (2013.01); *A61M 16/0488* (2013.01);
(Continued)

(58) Field of Classification Search
CPC .......... A61B 17/1204; A61B 17/12099; A61B 17/12104; A61B 17/12136;
(Continued)

(56) References Cited

U.S. PATENT DOCUMENTS 4,230,108 A    10/1980 Young
4,454,887 A *   6/1984 Kruger ............... A61B 1/00154
                                                128/207.14
(Continued)

FOREIGN PATENT DOCUMENTS

EP        2191792 A1    6/2010
WO     2014126723 A1    8/2014

OTHER PUBLICATIONS

Benington et al., "Preventing aspiration and regurgitation", Anaesthesia and Intensive Care Medicine, 2007, pp. 368-372, vol. 8, No. 9.
(Continued)

*Primary Examiner* — Colin W Stuart
*Assistant Examiner* — Matthew D Ziegler
(74) *Attorney, Agent, or Firm* — The Webb Law Firm

(57) ABSTRACT

A temporary esophagus occlusion device for providing temporary occlusion of the esophagus during intubation of a in patient includes a frame configured to transition between a contracted state, in which it can be swallowed by the patient, and an expanded state, wherein in the expanded state, the frame has a maximum outer diameter sufficient to span an inner diameter of the esophagus of the patient. The device also includes a flexible cover connected to and extending over at least a portion of the frame when the frame (Continued)

is in the expanded state to at least partially block flow of fluid and/or solid materials through the esophagus and a guidewire attached to the frame, sized to be swallowed by the patient along with the frame and having a proximal end portion configured to remain external to the patient's body and a distal end connected to the frame.

21 Claims, 11 Drawing Sheets

(52) U.S. Cl.
CPC ..... *A61B 17/1204* (2013.01); *A61B 17/12104* (2013.01); *A61M 25/0074* (2013.01); *A61M 2202/0403* (2013.01); *A61M 2205/0266* (2013.01); *A61M 2210/105* (2013.01); *A61M 2210/1053* (2013.01)

(58) Field of Classification Search
CPC ........ A61B 17/12172; A61B 17/12177; A61B 17/12022–12195; A61M 16/0409; A61M 16/0463; A61M 16/0488; A61M 25/0068; A61M 25/0074; A61M 2202/0403; A61M 2205/0266; A61M 2210/105; A61M 2210/1053; A61F 2/86–915
See application file for complete search history.

(56) References Cited

U.S. PATENT DOCUMENTS

| | | | |
|---|---|---|---|
| 5,305,740 | A | 4/1994 | Kolobow |
| 5,865,176 | A | 2/1999 | O'Neil |
| 6,635,068 | B1* | 10/2003 | Dubrul ............ A61B 17/12022 606/200 |
| 6,984,224 | B2* | 1/2006 | McKittrick ......... A61J 15/0026 604/270 |
| 7,175,660 | B2 | 2/2007 | Cartledge et al. |
| 7,762,261 | B1 | 7/2010 | Fortuna |
| 7,900,632 | B2 | 3/2011 | Cook |
| 8,162,969 | B2* | 4/2012 | Brister ................ A61B 90/39 606/196 |
| 8,251,067 | B2* | 8/2012 | Hendricksen ............ A61F 2/91 128/207.14 |
| 9,005,124 | B2 | 4/2015 | Addington et al. |
| 9,038,627 | B2 | 5/2015 | Chen |
| 9,114,033 | B2 | 8/2015 | Feld et al. |
| 9,138,338 | B2 | 9/2015 | Chambers et al. |
| 9,254,201 | B2 | 2/2016 | Ellsworth et al. |
| 9,254,213 | B2 | 2/2016 | Linder et al. |
| 9,265,905 | B2 | 2/2016 | Nasir et al. |
| 9,737,306 | B2* | 8/2017 | Rudakov ............ A61B 17/1214 |
| 2003/0144725 | A1* | 7/2003 | Lombardi ................. A61F 2/07 623/1.13 |
| 2004/0199202 | A1* | 10/2004 | Dubrul .................. A61B 90/39 606/191 |
| 2005/0245788 | A1 | 11/2005 | Gerber |
| 2006/0032505 | A1 | 2/2006 | Alfery et al. |
| 2006/0135947 | A1* | 6/2006 | Soltesz ............ A61B 17/12159 604/516 |
| 2008/0041392 | A1 | 2/2008 | Cook |
| 2010/0242957 | A1 | 9/2010 | Fortuna |
| 2011/0208011 | A1 | 8/2011 | Ben-Horin |
| 2013/0092172 | A1 | 4/2013 | Nasir et al. |
| 2015/0305903 | A1 | 10/2015 | Kitaoka |
| 2015/0366690 | A1 | 12/2015 | Lumauig |
| 2016/0067064 | A1 | 3/2016 | Vinluan et al. |
| 2018/0344991 | A1* | 12/2018 | Cerchiari ......... A61B 17/12136 |

OTHER PUBLICATIONS

Bernardini et al., "Risk of pulmonary aspiration with laryngeal mask airway and tracheal tube: analysis on 65,712 procedures with positive pressure ventilation", Anaesthesia, 2009, pp. 1289-1294, vol. 64, No. 12.

Cook et al., "Complications and failure of airway management", British Journal of Anaesthesia, 2012, pp. i68-i85, vol. 109, No. S1.

Cullen et al., "Results from the National Survey of Ambulatory Surgery (NSAS)", 2008, 50 pages.

Cullen et al., "Ambulatory Surgery in the United States, 2006", National Health Statistics Reports, 2009, 28 pages, No. 11.

Czarnetzki et al., "Erythromycin for Gastric Emptying in Patients Undergoing General Anesthesia for Emergency Surgery a Randomized Clinical Trial", JAMA Surgery, 2015, pp. 730-737, vol. 150, No. 8.

Graterol et al., "Pulmonary Aspiration", Anesthesia and Intensive Care Medicine, 2010, pp. 447-448, vol. 11, No. 10.

Kanich et al., "Altered Mental Status: Evaluation and Etiology in the ED", American Journal of Emergency Medicine, 2002, pp. 613-617, vol. 20, No. 7.

Kirtania et al., "Esophageal Guidewire-Assisted Nasogastric Tube Insertion in Anesthetized and Intubated Patients: A Prospective Randomized Controlled Study", Anesthesia & Analgesia, 2012, pp. 343-348, vol. 114, No. 2.

Marik, "Aspiration Pneumonia and Pneumonitis", Handbook of Evidence-Based Critical Care, 2010, pp. 233-244.

Robinson et al., "Aspiration under anaesthesia: risk assessment and decision making", Continuing Education in Anaesthesia, Critical Care & Pain, 2014, pp. 171-175, vol. 4, No. 4.

Sakai et al., "The Incidence and Outcome of Perioperative Pulmonary Aspiration in a University Hospital: A 4-Year Retrospective Analysis", Anesthesia & Analgesia, 2006, pp. 941-947, vol. 103, No. 4.

Thibodeau et al., "Incidence of Aspiration After Urgent Intubation", American Journal of Emergency Medicine, 1997, pp. 562-565, vol. 15, No. 6.

Warner et al., "Clinical Significance of Pulmonary Aspiration during the Perioperative Period", Anesthesiology, 1993, pp. 56-62, vol. 78, No. 1.

Xue et al., "Dynamics of Elective Case Cancellation for Inpatient and Outpatient in an Academic Center", Journal of Anesthesia and Clinical Research, 2013, 10 pages, vol. 4, No. 5.

* cited by examiner

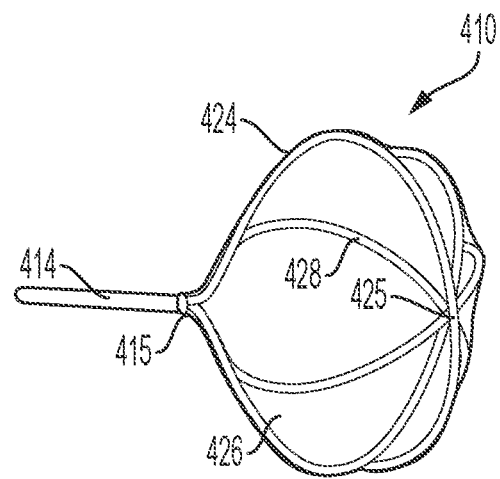 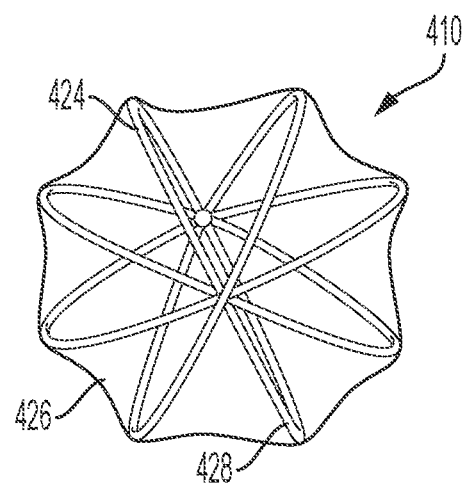
FIG. 5A  FIG. 5B
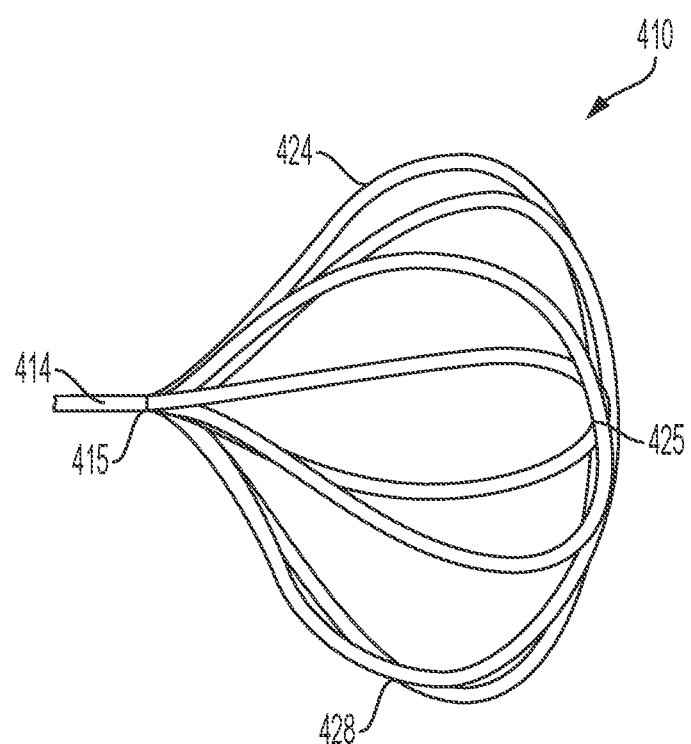
FIG. 5C

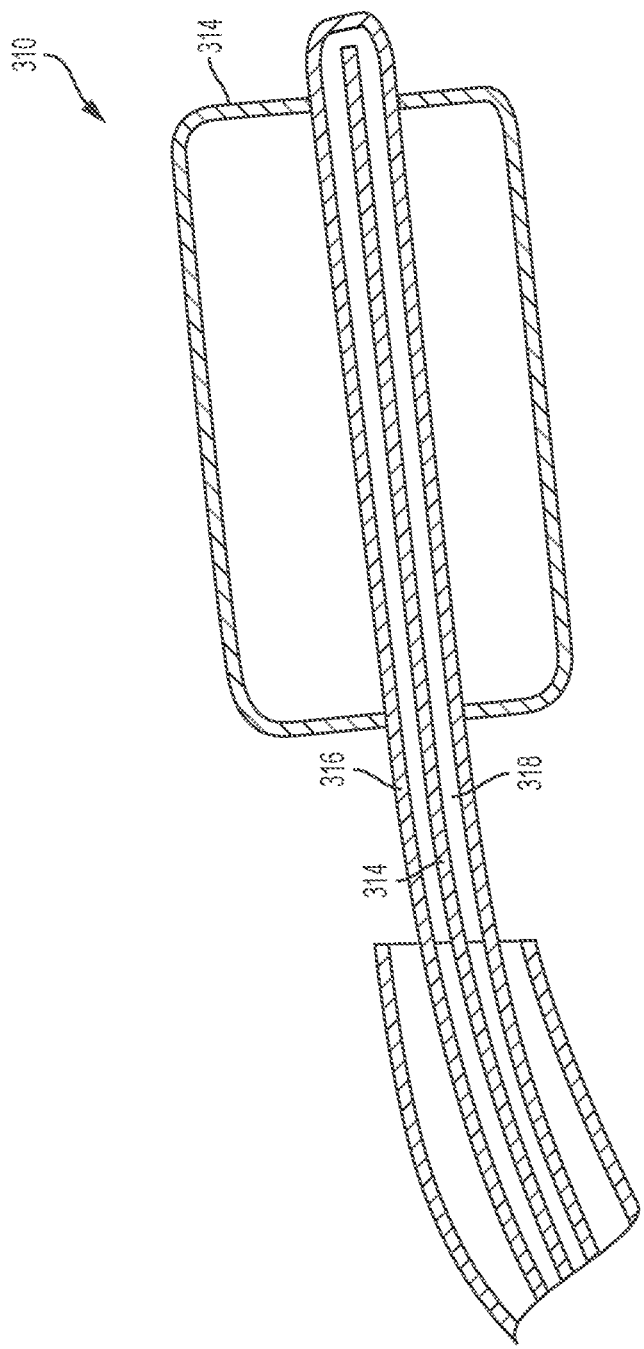

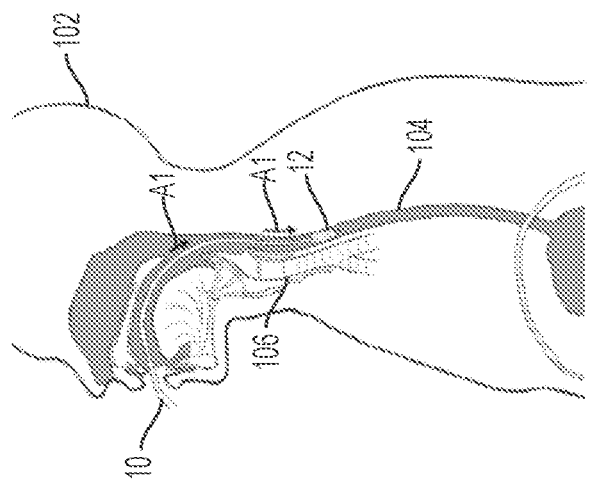
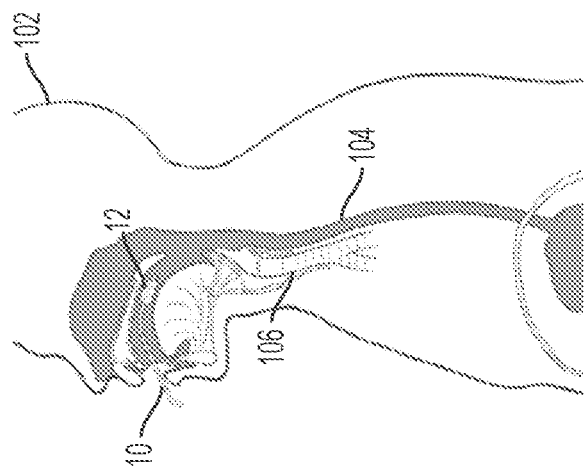

ESOPHAGEAL TEMPORARY OCCLUSION DEVICE AND METHOD FOR ENDOTRACHEAL INTUBATION AND OROGASTRIC TUBE INSERTION

CROSS REFERENCE TO RELATED APPLICATION

The present application is the United States national phase of International Application No. PCT/US2017/057139 filed Oct. 18, 2017, and claims the benefit of U.S. Provisional Patent Application Ser. No. 62/409,455, filed Oct. 18, 2016, the entire disclosure of each of which is hereby incorporated by reference.

BACKGROUND

Technical Field

The present disclosure relates to devices and methods for assisting in insertion and placement of an endotracheal or orogastric tube and, in particular, to a device and method for providing temporary occlusion of the esophagus device prior to intubation of the lungs or stomach.

Description of Related Art

Medical devices constructed to enter the trachea, esophagus, stomach, and lungs have been designed to meet a variety of medical needs. These needs include establishing airways for mechanical ventilation, stabilizing luminal patency during neoplastic growth, and insertion of imaging devices to monitor for pathology throughout the digestive system.

One such medical device is an endotracheal tube. An endotracheal tube is a hollow tube configured to be inserted in the trachea. The endotracheal tube includes an inflatable cuff that provides a tight seal around adjacent tissue and improves delivery of air and drugs to the lungs. As discussed herein, the cuff also protects the lungs from aspirated gastric juices. In order to place an endotracheal tube, the following steps may be followed in a surgical setting. First, once checked in for surgery, the patient is brought to the preoperative holding area. The patient is assessed by the anesthesia team and then taken the operating room (OR), transitioned to the OR table, and connected to various monitors. Once settled, medications are given to sedate the patient in preparation for breathing tube placement. The tube is then placed via a procedure known as direct laryngoscopy. During this procedure, the vocal cords are visualized and the breathing tube is positioned such that the tip of the tube sits several centimeters past the cords. Visualizing the vocal cords confirms that the tube is in the lungs and not the esophagus. Once in the correct position, the balloon or cuff at the end of the tube is inflated which provides a tight seal for the lungs to be inflated by a ventilator machine. Once the breathing tube is placed and the balloon or cuff is inflated, it is generally accepted that the patient is being protected from gastric aspiration.

A medical device that can be placed in the esophagus or stomach through the mouth is an orogastric tube. An orogastric tube is a hollowed-out, flexible rubber tube that is inserted into a patient's mouth and then manually pushed into the stomach. This procedure tends to be very uncomfortable and causes gagging, coughing, and occasionally vomiting. It is consistently rated as one of the most unpleasant procedures by patients. Since the orogastric tube is manually pushed down the patient's throat, it often enters the lungs instead of the stomach, which causes coughing. The tube can also coil in the back of the throat since there is no guidance for the tube as it travels towards the stomach via the esophagus. Once the tube is in place, a medical provider can use it to provide nutrition and medications. It is also used to suction out the stomach contents in patients with a variety of medical conditions.

Since most surgeries are scheduled well in advance, patients and physicians are able to develop a plan for the morning of surgery, which can address some problems of tube placement. Such plans often include which medications the patient should take, as well as direction to abstain from eating. The purpose of fasting is to reduce the risk of gastric contents causing lung injury during the procedure. Injuries from gastric contents can occur at any time during surgery, but are most often considered during placement of the breathing tube.

Patients needing emergency intubation can either be unconscious or conscious depending upon severity of the patient's illness or injury. Unconscious patients are likely to have aspirated gastric contents into their lungs even before the intubation procedure takes place. Conscious patients on the other hand are at high-risk between the time of sedation and breathing tube placement. This is because sedation medications indirectly promotes gastric aspiration by relaxing the smooth muscle in the stomach and esophagus. Further, since emergency intubations are unplanned, there is no time to implement a plan for addressing problems of tube placement, as occurs during scheduled surgeries. Further, current methods to minimize aspiration during the emergency intubations can be unreliable, time consuming, and/or uncomfortable for the patient.

For example, a method known as Rapid Sequence Induction (RSI) is the standard procedure used for intubation in emergency situations in the United States and Europe. What separates RSI from the standard method of intubation in elective surgeries is the speed at which everything occurs. RSI is done as quickly and as safely as possible to limit an amount of time in which injuries caused by gastric aspiration can occur. A practice known as "cricoid pressure" has also been developed, which attempts to provide protection against aspiration from the time a patient is sedated to the time of successful intubation. Applying cricoid pressure involves applying external pressure on the trachea to squeeze the esophagus shut. This physical maneuver was standard of care until studies showed that it does not reduce the risk of aspiration. As such, the practice of applying cricoid pressure during intubation is now less commonly used, although the need for protection against aspiration in RSI persists.

In addition to the practice of RSI, there are several other techniques to reduce the risk of aspiration in high-risk patients. These include nasogastric tube placement (NGT) and the use of gastric emptying drugs. The nasogastric tube is a long plastic tube that is manually inserted through a single nostril and threaded into the stomach. It is then connected to wall suction so that the stomach contents can be pumped out prior to sedation and intubation. There are several key problems with NGTs, the major one being that insertion of the tube is extremely uncomfortable for the awake patient and often induces gagging and vomiting. The tube is often misplaced into the lungs causing coughing which furthers the risk of gagging and vomiting.

Gastric emptying drugs can be given intravenously and help the stomach move contents into the small intestine by speeding up motility in the gastrointestinal tract. These drugs are given at least 15 minutes before intubation and have a significant side effect profile including nausea in 30% and stomach cramps in 23% of patients receiving the drugs. Furthermore, these drugs have also induced vomiting in a small percentage of patients.

Some anesthesiologists have also attempted to manually insert a guidewire into the stomach of a patient who was already under sedation and intubated. The anesthesiologists then threaded a gastric tube over the wire with success. However, this approach is only possible in patients that are already sedated; it is not applicable to the many patients that are awake, conscious, and need an endotracheal tube placed.

SUMMARY

In view of the difficulties in placing an endotracheal tube or orogastric tube for awake patients, medical devices and treatment methods are needed for facilitating tube placement in a safe and easy manner. The medical device and methods disclosed herein are designed to address these issues.

In accordance with an aspect of the disclosure, a temporary esophagus occlusion device for providing temporary occlusion of the esophagus during intubation of a patient includes a frame configured to transition between a contracted state, in which it can be swallowed by the patient, and an expanded state, wherein in the expanded state, the frame has a maximum outer diameter sufficient to span an inner diameter of the esophagus of the patient. The device also includes a flexible cover connected to and extending over at least a portion of the frame when the frame is in the expanded state to at least partially block flow of fluid and/or solid materials through the esophagus and a guidewire attached to the frame, sized to be swallowed by the patient along with the frame and having a proximal end portion configured to remain external to the patient's body and a distal end connected to a proximal end of the frame.

In accordance with another aspect of the disclosure, a method for deploying a temporary occlusion device in an esophagus of a conscious patient includes providing a temporary occlusion device. The temporary occlusion device includes an expandable frame configured to transition between a contracted state and an expanded state, wherein in the expanded state, the frame has a diameter sufficient to span an inner diameter of the esophagus of the patient, a flexible cover connected to and extending over at least a portion of the frame when the frame is in the expanded state, to at least partially block flow of fluid and/or solid materials through the esophagus, and a guidewire connected to the frame. The method further includes causing the patient to swallow the temporary occlusion device in the contracted state, such that a portion of the guidewire remains external to the patient's mouth and deploying the expandable frame at a desired position in the patient's esophagus, thereby at least partially sealing a portion of the patient's esophagus from gastric fluid from the patient's stomach.

In accordance with another aspect of the disclosure, a method for intubation of a patient with an endotracheal tube includes providing a temporary occlusion device. The temporary occlusion device includes an expandable frame configured to transition between a contracted state and an expanded state, wherein in the expanded state, the frame has a diameter sufficient to span an inner diameter of the esophagus of the patient, a flexible cover connected to and extending over at least a portion of the frame when the frame is in the expanded state to at least partially block flow of fluid and/or solid materials through the esophagus, and a guidewire connected to the frame. The method also includes causing the patient to swallow the temporary occlusion device in the contracted state, such that a portion of the guidewire remains external to the patient's mouth; deploying the expandable frame at a desired position in the patient's esophagus; after deployment of the expandable frame of the occlusion device, inserting a distal end of an endotracheal tube through the patient's mouth and into the patient's trachea or lungs; deploying a balloon or cuff of the endotracheal tube to at least partially seal the lungs and/or trachea; and removing the temporary occlusion device from the esophagus after the endotracheal tube is deployed.

In accordance with another aspect of the disclosure, a method for placement of an orogastric tube in a stomach of a patient includes: providing an anchor device comprising a guidewire and a wire frame mounted to a distal end of the guidewire; causing the patient to swallow the anchor device, such that a portion of the guidewire remains external to the patient's mouth; permitting the frame and guidewire connected thereto to advance to a desired position within the patient's esophagus; and advancing the orogastric tube over the guidewire and past the frame to position a distal end of the orogastric tube in the patient's stomach.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 5A is a photograph of a perspective view of another embodiment of a temporary occlusion device according to an aspect of the disclosure;

FIG. 5B is a photograph of a front view of the temporary occlusion device of FIG. 5A;

FIG. 5C is a photograph of a side view of a frame of the temporary occlusion device of FIG. 5A;

FIG. 6 is a cross-sectional view of another embodiment of a temporary occlusion device according to an aspect of the present disclosure;

FIGS. 7A to 7D are schematic drawings showing a method for insertion and deployment of a temporary occlusion device for providing temporary occlusion of the esophagus according to an aspect of the disclosure;

DETAILED DESCRIPTION

Figure 1:
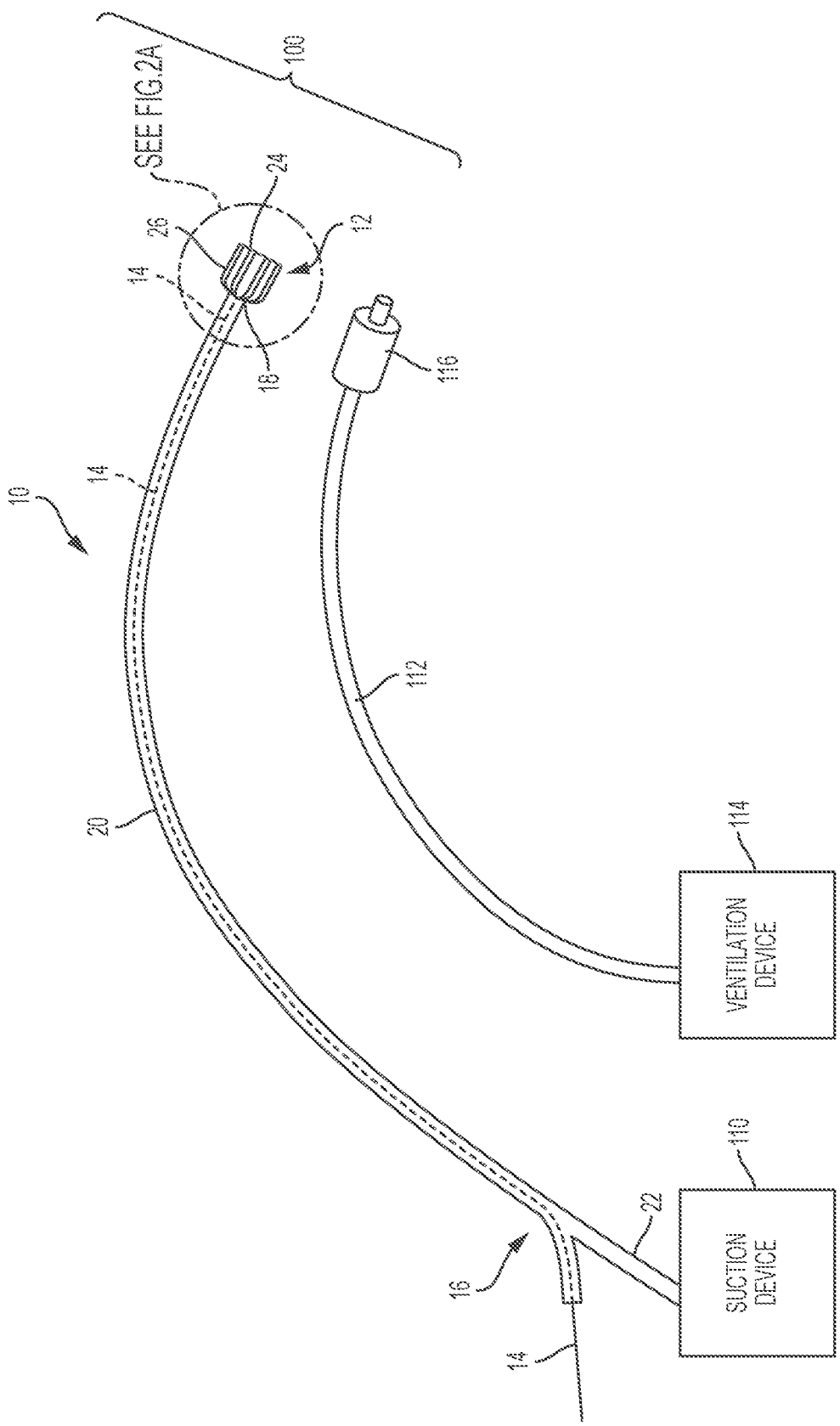
FIG. 1 is a schematic drawing of devices for providing temporary occlusion of the esophagus and breathing support or ventilation for a patient according to an aspect of the disclosure.

As used herein, the singular form of "a", "an", and "the" include plural referents unless the context clearly dictates otherwise.

As used herein, the terms "right", "left", "top", "bottom", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

An assembly 100 for providing temporary occlusion of a patient's esophagus during intubation is shown in FIG. 1. The assembly 100 includes a deployable temporary occlusion device 10 configured to be deployed in the esophagus to prevent gastric fluids and other materials from being drawn from the stomach and through the esophagus to the lungs. In general, the device 10 comprise an expandable portion 12 which, in a contracted or prior-to-use state, resembles a pill, capsule, tablet, or similar-sized structure attached to an elongated member, such as a guidewire 14. The expandable portion 12 of the device 10 is configured to be swallowed by a patient, such that the expandable portion 12 and guidewire 14 attached thereto advance through the patient's mouth and throat to the esophagus. As the patient is swallowing the expandable portion 12, a treating professional, such as a physician, may hold a proximal portion 16 of the guidewire 14 to control how far into the esophagus the device 10 descends or travels when swallowed. In order to assist in estimating a depth of the expandable portion 12 of the device 10, the guidewire 14 or a tube 20, enclosing a portion of the guidewire, can include marking bands or graduations which indicate distance from the distal end of the guidewire 14. Desirably, the expandable portion 12 of the device 10 is as small as possible, in the contracted state, so that it can be easily swallowed by the patient. For example, in the contracted state, the expandable portion 12 can be about 1.0 cm to 3.0 cm in length and about 1.0 cm or less in diameter. In the expanded state, the expandable portion 12 has a maximum diameter corresponding to an inner diameter of the esophagus. For example, the device 10 can have a maximum diameter from 2.0 cm to 4.0 cm and preferably about 3.0 cm in the expanded state.

In some examples, the guidewire 14 comprises a proximal end portion 16 configured to remain external to the patient's body and a distal end 18 configured for insertion into the body through the mouth. The guidewire 14 is generally long enough to extend from the patient's mouth through the throat and into a desired deployment location in the esophagus. In some examples, the guidewire 14 is between about 35 cm and 45 cm in length.

The assembly 100 further comprises the tube 20 or catheter extending over at least a portion of the elongated member or guidewire 14. The tube 20 can be any size tube suitable for insertion through the mouth and into the patient's stomach. If the tube is to be swallowed along with the expandable portion 12, then it should be as narrow as possible, preferably between about 1 Fr and 3 Fr, or less. As will be described herein, the occlusion device 10 can be at least partially enclosed within the tube 20 in a contracted state, which effectively counteracts a natural bias of the expandable portion 12 toward the expanded state. The tube 20 can also be used for providing certain therapies to the patient. For example, the tube 20 can be used as an orogastric tube for drawing fluids from the patient's stomach. In that case, a proximal end 22 of the tube configured to remain external from the patient's body is connected to a suction device 110, such as a vacuum pump. In other examples, the assembly 100 further includes a separate tube, such as an endotracheal tube 112 connected to a mechanical or manual ventilation device 114, such as a mechanical ventilator or manually activated ventilation bag, for providing breathing therapies to the patient's lungs. For example, once the temporary occlusion device 10 is properly deployed in the patient's esophagus, the patient can be safely ventilated by mask ventilation. Since the current standard of care for emergency intubation does not provide mechanical occlusion of the esophagus, it is not possible to perform mask ventilation safely with current technology.

The endotracheal tube 112 can be positioned within the patient's lungs in a conventional manner once the temporary occlusion device 10 is deployed in the patient's esophagus. As is known in the art, the endotracheal tube 112 can include an inflatable cuff 116 near a distal end thereof for sealing the trachea to assist in maintaining proper positioning of the tube 112.

More specifically, the temporary occlusion device 10 is configured to provide protection during intubation of an awake or conscious patient, as is often required in emergency situations, such as occurrences of traumas, appendicitis, worsening of severe heart or lung disease, and life-threatening infections. Other natural situations such as unplanned cesarean sections in the pregnant population may also warrant such a procedure. Patients suffering from these conditions are unlikely to have empty stomachs, so the risk of harm to the lungs from gastric contents is higher than normal. These patients are, therefore, considered high-risk for gastric aspiration. Gastric aspiration can be a devastating complication of procedures involving placement and positioning of orogastric and endotracheal devices. It can occur during intubation, as well as in many other clinical scenarios. There are several important risk factors for the development of aspiration and these include emergency situations, inadequate depth of anesthesia, abdominal pathology, obesity, an anatomically difficult airway, and the use of opioid medications. Aspiration is most likely to occur during breathing tube placement, but can occur at any time during a surgery including when the patient is waking up from anesthesia and even after the breathing tube is removed. It has been established in the medical literature that increased attempts at intubation (also known as failed intubation) are associated with increased medical complications. The rate of failed intubations is well-studied and has an incidence of: 1:50-100 in the emergency room and ICU; 1:1-2,000 in elective operating room cases; and 1:50-100 intubations in pregnancy. Reducing the number of failed attempts would improve the safety of intubation.

The mechanisms by which gastric aspiration causes injury to the lungs are three-fold. First, food particles can cause mechanical obstruction of lung tissue leading to elevated heart and breathing rate, low blood oxygen levels, and subsequent pneumonia. Second, the acidified gastric contents cause immediate corrosion of lung tissue and then a delayed inflammatory response that can take up to two weeks to appreciate clinically. Finally, bacteria from the stomach and esophagus, which are not normally present in the lungs, can cause infection in the areas damaged by acid corrosion. It is important to note that aspiration can be an active or passive process meaning it can be accompanied by retching and vomiting or can be a slow and unwitnessed trickling of fluid into the lungs from the esophagus.

Not all patients with an aspiration event develop symptoms, but depending on how the patient looks clinically, several investigative exams and procedures can be ordered to evaluate the severity of illness. These include chest radiographs, computed tomography, blood gas monitoring, sputum cultures, and bronchoscopy. Treatment options include antibiotics, steroids, and the potential need for intensive care unit monitoring. Long-term consequences of an aspiration event could include repeated lung infections. While not all patients that aspirate develop symptoms, it is estimated that 8 to 10% of patients with aspiration die from associated complications. See, Graterol and Clayton, "Pulmonary Aspiration", Anesthesia and Intensive Care. Pulmonary aspiration can occur when patients who have recently eaten require emergency endotracheal intubation. Several attempts may be required to successfully intubate the patient, during which time gastric contents can flow into the lungs, causing aspiration.

In some examples, the assemblies 100 and occlusion devices 10 described herein replace techniques such as applying cricoid pressure by providing temporary occlusion of the esophagus allowing for safer care and more time for providers to perform intubation. The physical location of the patient at the time that intubation is needed often dictates which health care provider will perform the procedure. These providers and locations include emergency medicine physicians in the emergency room, intensive care physicians in the ICU, and anesthesiologists in the operating room. It is important to note that different providers have varying levels of expertise performing intubation. In general, anesthesiologists are the physicians that perform intubation most frequently.

Exemplary Expandable Portions of Temporary Occlusion Devices

Figure 2A:
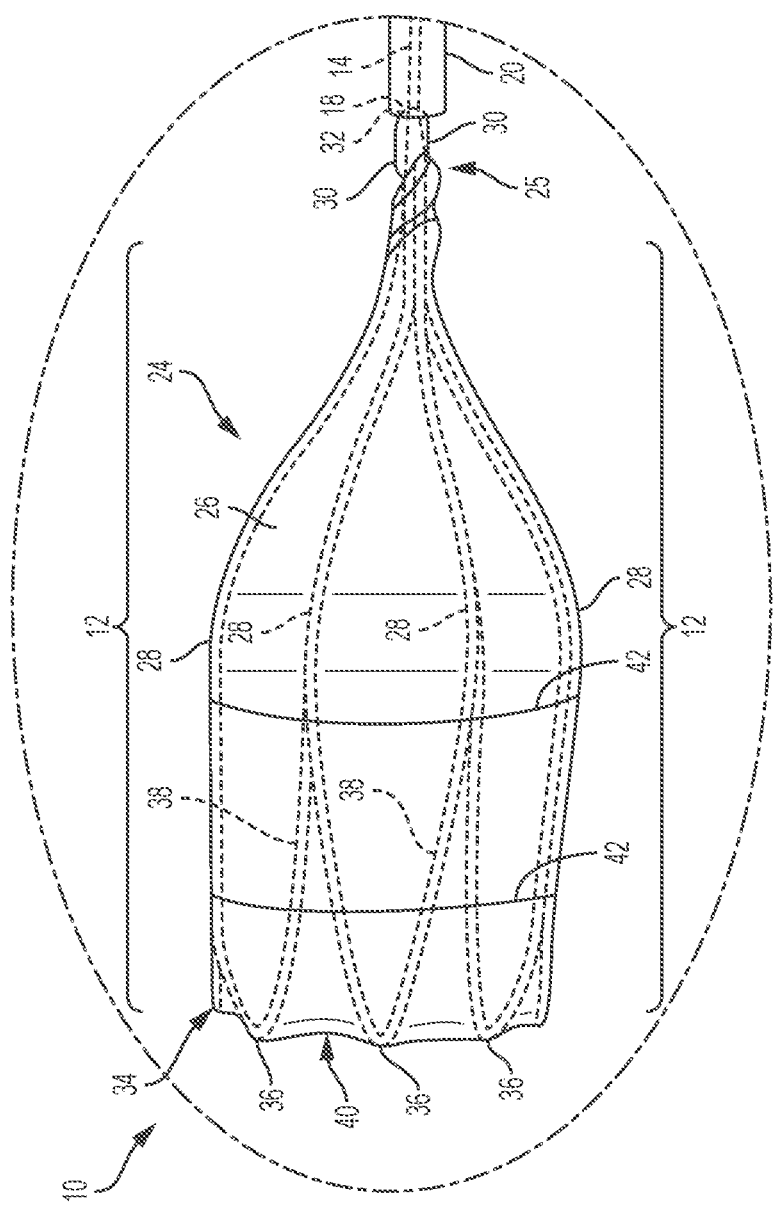
FIG. 2A is a side view of a portion of the temporary occlusion device of FIG. 1 enclosed by circle 2A.
Figure 2B:
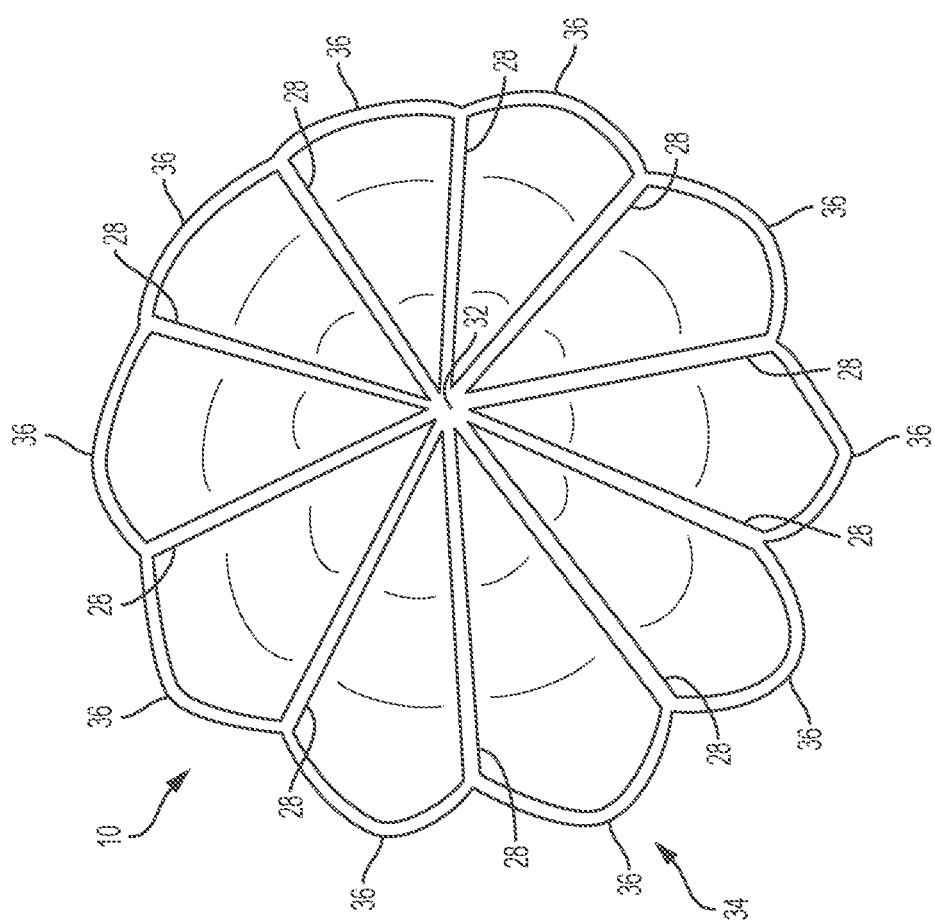
FIG. 2B is a front view of the temporary occlusion device of FIG. 2A.
Figure 3:
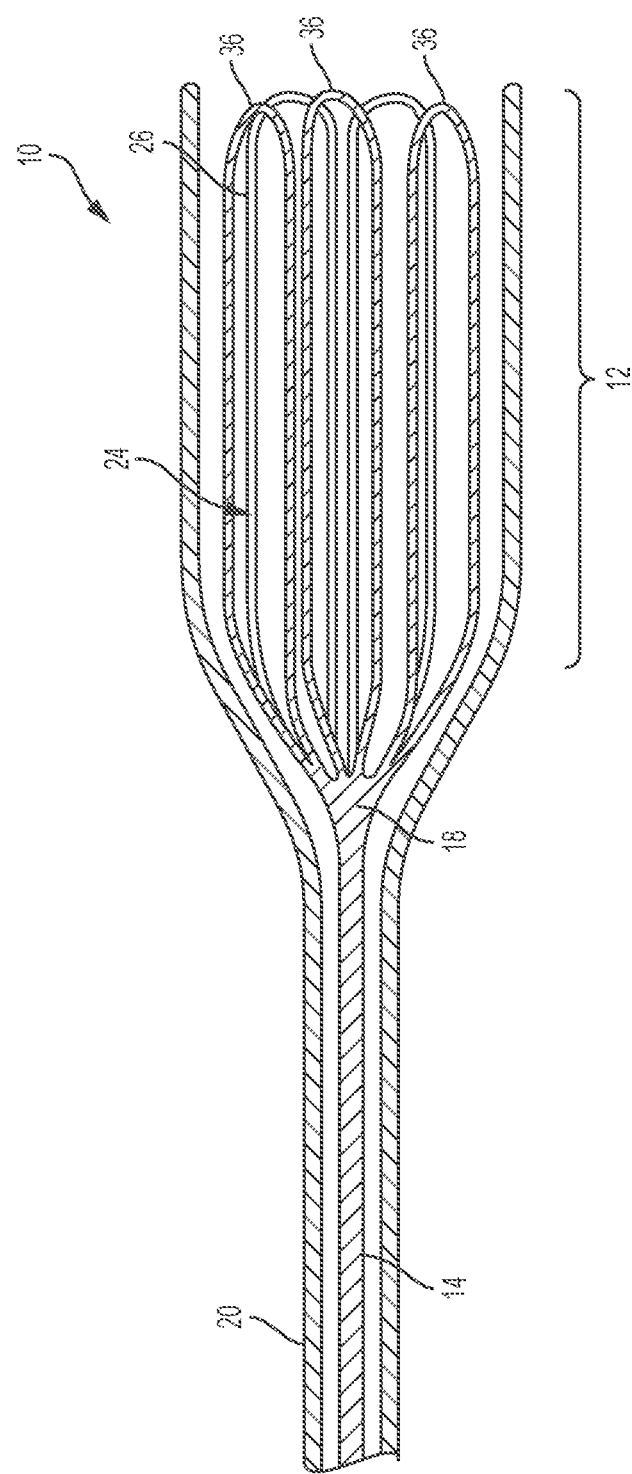
FIG. 3 is a cross sectional view of the temporary occlusion device of FIG. 1 in a collapsed position.

As shown in FIGS. 2A, 2B, and 3, the expandable portion 12 of the temporary occlusion device 10 comprises an expandable basket or frame 24 extending from the distal end 18 of the guidewire 14. The basket or frame 24 is configured to transition from the collapsed state (as shown in FIG. 3) to the expanded or deployed state (shown in FIGS. 2A and 2B), in which the frame 24 and device 10 occlude a portion of the esophagus. The device 10 further includes a filter or cover 26 supported by the basket or frame 24. When in the deployed position, the cover 26 and frame 24 are configured to block gastric fluids and solid particles from moving through the esophagus past the occlusion device 10. As such, the frame 24 and cover 26 can be configured to seal an interior wall of the esophagus to prevent substances from flowing past the occlusion device.

In some examples, the basket or frame 24 includes a plurality of tines or elongated members 28. The tines or elongated members 28 can be biased to the expanded position and, for example, can be maintained in the contracted position when the basket or frame 24 is positioned within the tube 20. The tines or elongated members 28 can be arranged in a variety of configurations generally having a diameter slightly larger than a diameter of a human esophagus and which provide sufficient support for the cover 26, when the basket or frame 24 is in its deployed position, to prevent the cover 26 and/or frame 24 from collapsing when exposed to pressure from the stomach or from airflow provided from an endotracheal tube.

In some examples, the elongated tines or elongated members 28 are formed from a flexible metallic material or from a shape-memory metallic material, e.g., a shape-memory metal, such as Nitinol. In some example, a thickness of the tines or elongated members 28 ranges from about 0.2 mm to 0.8 mm in diameter. In some cases, the tines or elongated members 28 are a constant thickness or diameter along their entire length. In other examples, proximal portions of the elongated members 28, which are less likely to be exposed to pressure caused by gastric fluid can be chemically etched to reduce thickness, so that they can adopted a smaller configured in the contracted state.

In some examples, the elongated members 28 are formed from a shape memory material, such as Nitinol. Nitinol is a nickel titanium alloy that has found broad use in a wide range of trans-catheter devices due to its shape memory property. The shape memory response for Nitinol is defined as a mechanical deformation in a low temperature state (martensite) with deformations fully recovered when the material is heated to body temperature (austenite). This shape memory behavior is useful for trans-catheter devices because Nitinol structures can easily be collapsed into a small diameter catheter in its martensite phase. Upon exposure to blood temperature, the Nitinol structure deploys spontaneously to its original shape (the austenite phase).

In some examples, the guidewire 14, which is connected to the proximal end 25 of the frame 24, is a conventional guidewire, such as a 1 Fr, 2 Fr, or 3 Fr guidewire, having an outer diameter of between about 0.33 mm and 1.0 mm, formed from a flexible metallic material, as is used for positioning catheters and medical devices in different locations in a patient's body. In other examples, the guidewire 14 can be an ultrathin guidewire having an outer diameter of between 0.02 mm and 0.1 mm to permit easier swallowing.

In some examples, the guidewire 14 can be tapered such that proximal portions of the guidewire 14, which remain external to the body, are thicker than distal portions of the guidewire 14 adjacent to the frame 24. Desirably, the guidewire is as thin and flexible as possible so that it can be easily swallowed along with the pill or expandable portion of the device, while maintaining sufficient strength and rigidity so that the guidewire 14 can be used to pull the device 10 from the patient's mouth after use.

The filter or cover 26 of the device 10 is generally formed from a flexible sheet or substrate wrapped around an outer portion of the basket or frame 24. In some examples, as shown in FIGS. 2A and 2B, the cover 26 encloses the entire frame 24, extending across a distally facing opening 40 thereof, and is connected or cinched to the frame 24 near the proximal end 25. For example, wire filaments, polymer filaments, or adhesives can be used for connecting portions of the cover 26 to the frame 24. In other examples, the cover 26 is only connected to distal portions of the frame 24 leaving proximal portions of the frame 24 uncovered.

The cover 26 is formed from a sheet of a thin, flexible polymer material, such as polyester or expanded polytetrafluoroethylene (ePTFE). For example, the cover 26 can be a flexible ePTFE sheet between about 80 μm and 120 μm thick, and preferably about 100 μm thick. The sheet may also be formed from other suitable materials capable of blocking gastric fluids from traveling through the esophagus past the deployed device 10. For example, flexible sheets formed from other water-repellant polymer materials may also be used for the cover 26 within the scope of the present disclosure.

As shown in FIGS. 2A and 2B, in some examples, the tines or elongated members 28 are arranged in a tulip-shaped configuration in which end portions 30 of the elongated members 24 are joined together to form wire pairs. For example, separate wire filaments could be wound or otherwise attached together to form the pairs. In other examples, the pairs could be integrally formed structures that separate at a mid-point 38 to form adjacent portions of the tulip structure. In some examples, the elongated members 28 are bent to form a plurality of circumferentially disposed petal-shaped lattices having a tip 36 at the distal end 34 of the frame 24. The petal shaped lattices can extend longitudinally from the distal end 18 of the guidewire 14, thereby forming the tulip-shaped structure and the distally facing opening 40.

In some examples, the end portions 30 of the elongated members 28 or wire pairs are connected to the guidewire 14 at a connection point or hub 32. Generally, the end portions 30 of the elongated members 28 are connected to the guidewire 14 by welding, soldering, or using one or more adhesives or fasteners. More specifically, connections between metallic (e.g., Nitinol) structures can be manufactured via one or more of (1) micro laser welding by aligning two Nitinol wires in parallel and (2) mechanical clamping using thin wall Nitinol tubes. For the micro laser welding, applied power can be from 0.8 to 1.5 kW, spot size can be from 0.3 mm to 1.0 mm, excitation time can be from 0.8 to 3.0 ms, and frequency can be from 1 to 5 Hz. For the mechanical clamping method, two wires are inserted into short thin wall Nitinol tube from opposite directions until the wires touch together. The Nitinol tube diameter is almost identical to the inserted wires; therefore, a tight connection can be obtained. In other examples, a biocompatible glue can be used inside the Nitinol tube if needed. In some examples, adhesive tape may be positioned around the connection point or hub to reinforce the connection between the tines and guidewire.

In some examples, the frame 24 may also include one or more circumferential struts 42 extending around the petal shaped lattices for providing additional support for the cover 26. In one example, as shown in FIGS. 2A and 2B, the struts 42 are circular. In other examples, the struts may be bent in a zig-zag pattern or wave-like pattern. In other examples, the struts 42 could be in a helical configuration wrapped around the lattices formed by the elongated members 28.

As discussed in further detail herein, other collapsible geometries are also contemplated within the scope of the present disclosure, considering the vast number of self-expanding basket, anchor, and filter geometries known to those of ordinary skill in the art. For example, rather than bending elongated members 28 to form the tulip-shaped lattices, distal ends of circumferentially adjacent elongated members 28 could be joined together near the distal end 34 of the frame 24 by a suitable fabrication technique to form the petal shaped lattices. In other examples, the basket or frame 24 can have any of a variety of low density expanded structures suitable for insertion within a small diameter catheter and having a large expanded diameter that corresponds to a diameter of the inner diameter of the esophagus. A "low density structure" refers to a structure in which a volume of the elements that form the structure is substantially less than a volume of the structure (e.g., a volume defined between the inner surface and the outer surface of the frame 24). It also is desirable to avoid undue radial pressure on the existing valve annulus, which also favors a lower density structure.

In order to maintain the occlusion device 10 in its contracted state prior to use and as it is being swallowed, the occlusion device 10 can be enclosed and mechanically constrained within an elongated tube or shaft, such as the tube 20 extending over the guidewire 14. In some examples, as shown in FIG. 1, the tube 20 extends over the guidewire for a majority of the guidewire length. Accordingly, when the occlusion device 10 is deployed in the esophagus, the tube extends over the guidewire, such that a proximal end of the tube 20 is positioned outside of the patient's mouth, and the distal end of the tube is positioned in the esophagus adjacent to the proximal end or hub of the occlusion device. In some examples, the tube 20 has a substantially constant inner diameter and outer diameter along its entire length. In other examples, as shown in FIG. 3, a distal end portion of the tube has a slightly larger diameter than other portions of the tube 20 to receive the collapsed occlusion device. More proximal portions of the tube 20, which enclose the guidewire rather than the frame 24, are narrower.

As discussed herein, in some examples, the patient swallows the entire device 10 including the frame 24 and cover 26, along with portions of the guidewire 14 and tube 20. Once swallowed, the frame 24 is deployed either by pushing the frame 24 out of the tube 20 using a pusher rod or by retracting the tube 20 to expose the expandable portion 12 of the device 10. The occlusion device 10 can be removed from the body by drawing the occlusion device 10 back into the tube 20, thereby causing the frame 24 to transition to the collapsed or contracted state. The tube 20, guidewire 14, and contracted frame 24 can then be removed by drawing them from the body through the patient's mouth.

In other examples, only the guidewire 14 and frame 24 are swallowed. In that case, the frame 24 can be maintained in the contracted state by some other mechanical structure. For example, the frame 24 can be enclosed within a dissolvable capsule. In other examples, the frame 24 can be configured to remain in its contracted state until the elongated members 28 are exposed to an activating condition, such as when the elongated members 28 are warmed to body temperature. Once the elongated members 28 warm to body temperature, the frame 24 can be configured to automatically transition to the expanded state. In these examples, the tube 20 can be advanced to the location of the occlusion device 10 over the guidewire 14 after the occlusion device 10 is deployed. Once in place, the tube 20 can be used for applying suction to the esophagus or stomach to draw fluids therefrom. In that case, the tube 20 can be a low-profile suction or orogastric tube having multiple fenestrations (e.g., openings or perforations) along a distal end portion thereof. When the device 10 is in the expanded or deployed state in the esophagus of the patient, the distal end of the tube 20 can be advanced to the frame 24. Once the tube 20 is in place, suction can be applied to prevent high pressure build-up caused by placement of the device 10. The tube 20 can also be used for removal of the device 10 as described above.

Figure 4A:
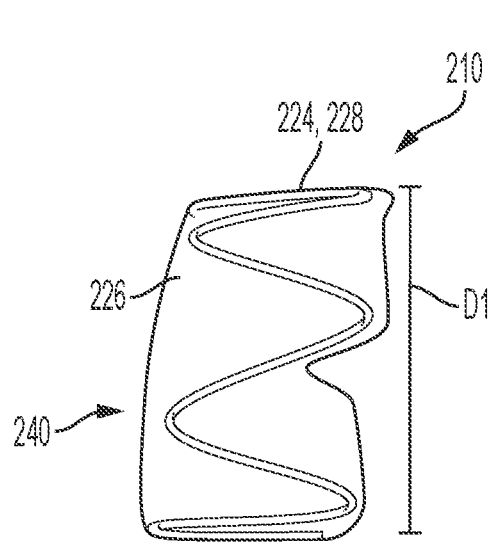
FIG. 4A is a photograph of a front view of another embodiment of a temporary occlusion device according to an aspect of the disclosure.
Figure 4B:
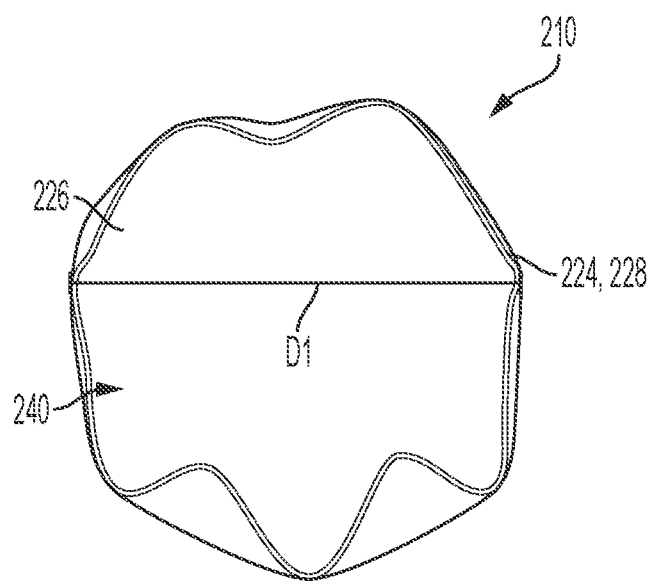
FIG. 4B is a photograph of a side view of the temporary occlusion device of FIG. 4A.
Figure 4C:
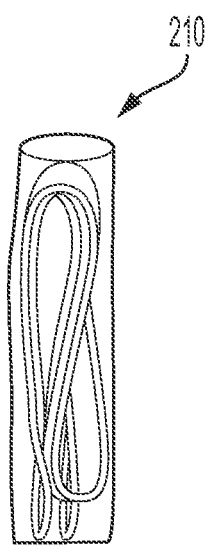
FIG. 4C is a photograph of a side view of the temporary occlusion device of FIG. 4A in a contracted state.

With reference to FIGS. 4A-4C, another embodiment of an esophagus deployment device 210 is illustrated. As in the previously described examples, the deployment device 210 includes a frame 224 formed from flexible elongated members, which can be transitioned between a contracted state (as shown in FIG. 4C) and an expanded state (as shown in FIGS. 4A and 4B). Specifically, as shown in FIGS. 4A and 4B, the frame 224 has a zig-zag pattern formed by an annular member 228 with upwardly and downwardly directed portions forming the zig-zag. The annular member 228 has a diameter D1 which corresponds to an inner diameter of the esophagus. For example, the diameter D1 of the annular member 228 can be between about 2.0 cm and 4.0 cm, and preferably about 3.0 cm. As in previous examples, the annular member 228 can be connected to a guidewire, such as by two or more radially and axially extending members or struts (not shown). For example, the struts can be connected to a portion of the annular member 228 by welding or a similar adhering technique. As in the previous examples, a cover 226 is mounted to the frame 224. For example, the cover 226 can extend across an opening 240 defined by the annular member 228 such that, in the deployed position, the device 210 and cover 226 occludes all, or at least a substantial portion, of the esophagus.

With reference to FIGS. 5A-5C, another embodiment of an esophagus deployment device 410 is illustrated. The deployment device 410 includes a ball or teardrop shaped frame 424 formed from a plurality of elongated members 428. As in previous examples, the elongated members 428 can be formed from a flexible metal material, such as Nitinol. As shown in FIGS. 5A-5C, opposing ends of the elongated members 428 are connected to or integrally formed with a distal end 415 of a guidewire 414. The elongated members 428 extend radially and axially from the guidewire 414 forming loops which intersect or cross over each other at a distal end 425 of the frame 224. As in previous examples, the frame 424 is sized to span the esophagus in a deployed state. Accordingly, the frame 424 has a maximum outer diameter which corresponds to an inner diameter of the esophagus. For example, the maximum outer diameter can be between about 2.0 cm and 4.0 cm, and preferably about 3.0 cm. As shown in FIGS. 5A and 5B, a cover 426 is mounted to or supported by the frame 424. For example, the cover 426 can be attached on an inside portion of the frame 424 and can extend between adjacent elongated members 428, such that in a deployed state, the cover 426 substantially occludes a patient's esophagus. In other examples, the cover 426 can be wrapped around or extend over the frame 426. In either case, the cover 426 can be connected to the elongated members 428 of the frame 424 by a mechanical fastener such as wire thread or staples, heating or annealing, or using a biocompatible adhesive, as is known in the art.

With reference to FIG. 6, in another example, the occlusion device 310 includes an expandable balloon 312 rather than a frame 324 or basket. For example, the balloon 312 can include a hollow body enclosing an interior. The body can be any shape suitable for occluding all or a substantial portion of the esophagus including, for example, cylindrical, spherical, teardrop, funnel, or oblong. The balloon 312 can be transitioned to an inflated or expanded state by filling the interior with a liquid (e.g., saline solution) or air. As in previous examples, the balloon 312 can be connected to a guidewire 314 for controlling a position or depth of the device 310 in the esophagus and for removing the device 310 from the patient's mouth after a procedure has been performed. The device 310 can also include an inflation tube 316 defining an inflation lumen 318 extending along the guidewire 314. The inflation lumen 318 can be in fluid communication with the interior of the balloon 312 for inflating and deflating the balloon. The device 310 can also include an outer tube 320, such as a catheter or sleeve, which encloses the guidewire 314 and inflation tube 316 so that these structures can be easily removed from the patient's mouth after use. As discussed herein, the outer tube 320 can also be used as an orogastric tube when suction is applied thereto.

Use and Deployment of the Occlusion Device

Figure 7D:
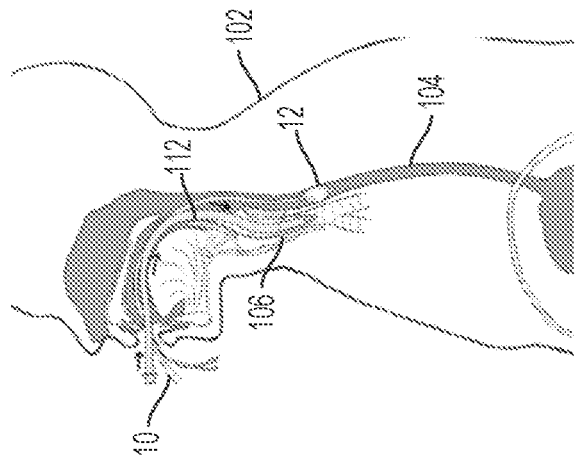

Having described the structure of a number of different examples of an occlusion device 10, 210, 310, 410, steps for deployment and use of the device will be described in detail with specific reference to FIGS. 7A-7D. In use, as shown in FIG. 7A, the patient 102 swallows the expandable portion 12 of the device 10 along with a portion of the guidewire 14 and tube 20 (shown in FIGS. 1-3). Other portions of the device 10 remain external to the body. In this sense, the device 10 resembles a "pill attached to a string" with the "pill" being the frame and distal portions of the tube. Generally, once the 'pill' portion is swallowed, it makes its way to the stomach by taking advantage of the natural physiology and swallowing mechanism. For example, as when a patient swallows food, the natural swallowing reflex becomes activated, so the device 10 enters the stomach and not the lungs.

As shown in 7B, after swallowing, the temporary occlusion device 10 descends into the esophagus 104 as shown by arrow A1. The distance from the upper central incisors to the junction of the esophagus and stomach (GE junction) is between 35 cm and 45 cm or about 40 cm. The distance from the incisors to the site of endotracheal intubation in the lungs ranges from about 15 cm to 20 cm. In some examples, the temporary occlusion device 10 is desirably deployed above the GE junction and below a placement site for an endotracheal tube 112 (shown in FIG. 7D), a target range from 20 cm to 40 cm from the upper teeth. Since there is a muscular sphincter that separates the GE junction, the device 10 is desirably deployed in the esophagus and not within the muscular sphincter or the stomach. For these reasons, the optimal region of deployment ranges from about 20 cm to 35 cm from the upper teeth. Average transport time from the time the device is swallowed is around 10 seconds to 15 seconds, which is sufficient time to deploy device.

Figure 7C:
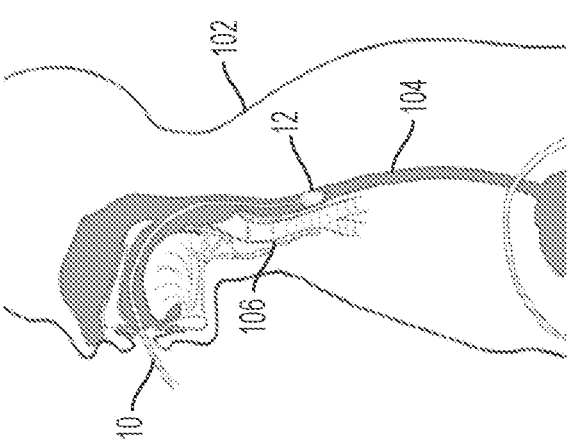

As shown in FIG. 7C, the occlusion device 10 is deployed in the esophagus 104 by expanding the frame 24 or basket. The patient 102 is then sedated and, as shown in FIG. 7D, the endotracheal tube 112 is inserted into the patient's trachea 106 or lungs in a conventional manner, as is known in the art. Once the endotracheal tube 112 is in place, the temporary occlusion device 10 can, optionally, be removed. For example, the frame 24 and cover 26 of the device 10 can be moved back to the collapsed state. In most examples, the frame 24 and cover 26 are collapsed by drawing the frame into the tube 20, thereby causing the frame 24 to contract due to contact with the inner wall of the tube 20. The entire assembly including the outer tube 20, frame 24, and guidewire 14 can then be removed from the body through the patient's mouth.

In other examples, the expandable portion 12 of the device 10 can be collapsed or retracted by removing or adjusting an activating condition to cause the tines or elongated members of the frame 24 to return to the contracted state. For example, for frames 24 formed from shape memory metals, contacting the frame 24 with a cold liquid would cause the elongated members to return to the contracted state. In that case, in order to contract the frame 24, cold water could be introduced to the esophagus through the tube 20. Once exposed to the cold water, the frame 24 may pull away from the inner wall of the esophagus 104 making removal of the device easier than if the elongated members or tines of the frame 24 were fully extended. It is noted that the frame 24 does not necessarily need to contract all the way to its initial size, since it is not being swallowed. Instead, the frame 24 may only need to contract by about 50% or less compared to its expanded state. For example, reducing the outermost diameter to between 2.0 cm and 2.5 cm may be sufficient for removal through the patient's mouth.

Orogastric Tube Placement

According to other aspects of the present disclosure, a swallowed guidewire can also be used for positioning an orogastric tube in the patient's esophagus. A benefit of having the guidewire in the esophagus means no more inadvertent insertions of the orogastric tube into the lungs, less vomiting, and no more coiling of the orogastric tube. As was the case for the endotracheal tube placement method, placement of the orogastric tube using a swallowed guidewire requires that the patient be conscious and able to participate in his or her care. Examples of patients that could participate in their care include patients needing abdominal/pelvic surgery (e.g., appendicitis, bowel obstruction, ovarian surgery), repair of broken limbs due to trauma, and women requiring emergency caesarean section.

In order to position the orogastric tube, the patient swallows an anchor device or stent connected to the guidewire. In some examples, the anchor device is an expandable temporary occlusion device, such as the devices shown in FIGS. 1-6. In that case, the temporary occlusion device is swallowed in its contracted state. In other examples, since the anchor device is used for providing a guide for orograstric tube placement and not for sealing the esophagus, the anchor device can be a smaller stent structure. For example, the anchor device can be an expanded stent attached to the distal end of the guidewire having a maximum outer diameter of about 1.0 cm or less, so that it can be easily swallowed in its expanded state.

As in previous examples, the anchor device and guidewire attached thereto passes through the mouth and throat into the esophagus. A depth of the anchor device in the esophagus is monitored by observing how much of the guidewire remains outside of the patient's mouth. When an expandable temporary occlusion device is used, it can be deployed at the desired position in the esophagus as described herein. When using an expanded stent, no deployment within the esophagus is required.

Once the anchor device is in place (e.g., at a desired depth within the esophagus), the orogastric tube can be advanced to the esophagus over the guidewire. When using the expanded stent, the orogastric tube can pass over the stent and through the esophagus into the stomach. When using a temporary occlusion device, the temporary occlusion device may need to be contracted so that the orogastric tube can pass over it. For example, the guidewire and device can be pulled through an open distal end of the orogastric tube, while leaving the orogastric tube in place in the esophagus. Once the temporary occlusion device is removed, the orogastric tube can be advanced through the esophagus into the stomach.

Fabrication Method

In some examples, in order to make the device, first, Nitinol frames are manufactured using a micro laser welding after precise mechanical bending processes. Subsequently, a thermal annealing process (e.g., quenching process) is performed to obtain the super-elastic property in the body temperature. In one example, the Nitinol frame is mounted to a mandrel (e.g., an aluminum mandrel), such as a rigid metallic disk or sphere. Both the aluminum sphere and disk can be used as a mandrel for manufacturing a ball shape and oval shape of baskets, respectively. In some examples, the Nitinol wires are pre-shaped with the aluminum mandrel prepared via machining processes such as turning, milling, drilling, and polishing. Then, the mandrel that contains the Nitinol wires is thermally treated in 500° C. for 30 min and subsequently cooled down in 20° C. DI water for 5 min (i.e. quenching). After removal of the Nitinol wire from the mandrel, the extension wires can be connected by either a micro laser welding process or mechanical clamping using a thin wall Nitinol tube. After the frames are manufactured, thin covering membranes are attached using either polymer adhesive or fine sutures. In some examples, thin film Nitinol is fabricated by sputter deposition process and the polyester membrane is fabricated using electrospinning Both collapse and deployment tests were performed using transparent tubes to demonstrate the size reduction (i.e., currently 3 mm inner diameter) and the capability of deployment.

Testing Methods and Examples

Figure 8:
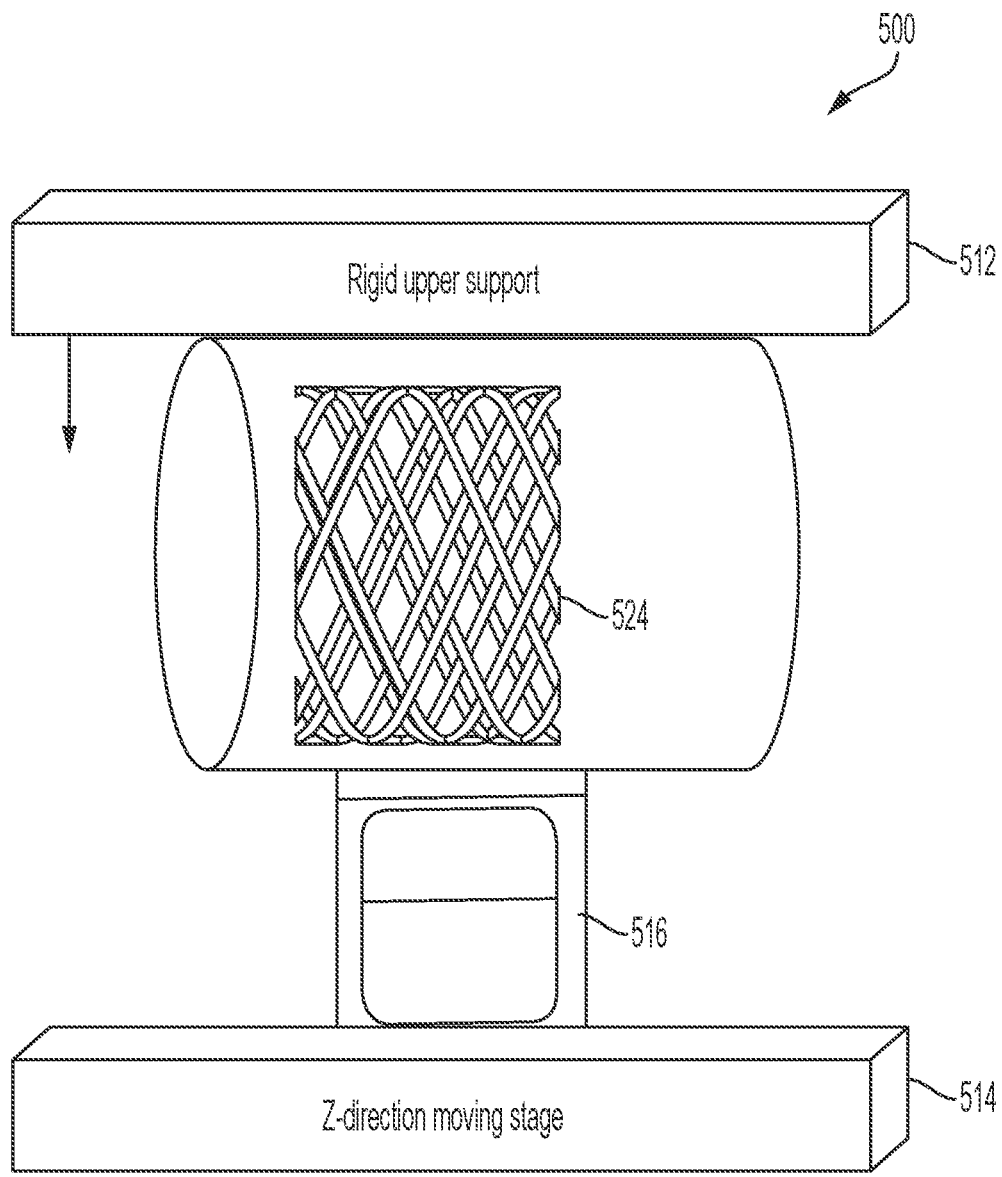
FIG. 8 is a schematic drawing of a testing procedure for evaluating radial force and potential leakage of an exemplary esophagus temporary occlusion device according to an aspect of the disclosure.

FIG. 8 shows a schematic drawing of in vitro custom-built test apparatus 500 for evaluating the radial force and potential leakage of an exemplary esophagus temporary occlusion device 10, as described herein. In one example, the super-elastic Nitinol frame 524 is deployed between two rigid supports 512, 514. The supports 512, 514 are moved to compress the frame 524 by an amount representative of pressure caused by gastric flow, for example, the frame 524 may be compressed by about 20%. A high precision load cell 516 measures the exerted radial force and transfers measured data to a computer for further analysis. A special scenario (e.g., a realistic situation) such as muscle expansion (e.g., wave-like) of the esophagus by sneezing may be considered and tested by increasing the radial force and contact area between the device and muscles. This test can be coupled with the extreme tube expansion and compression using a high pressure pump to optimize the device design.

Figure 9:
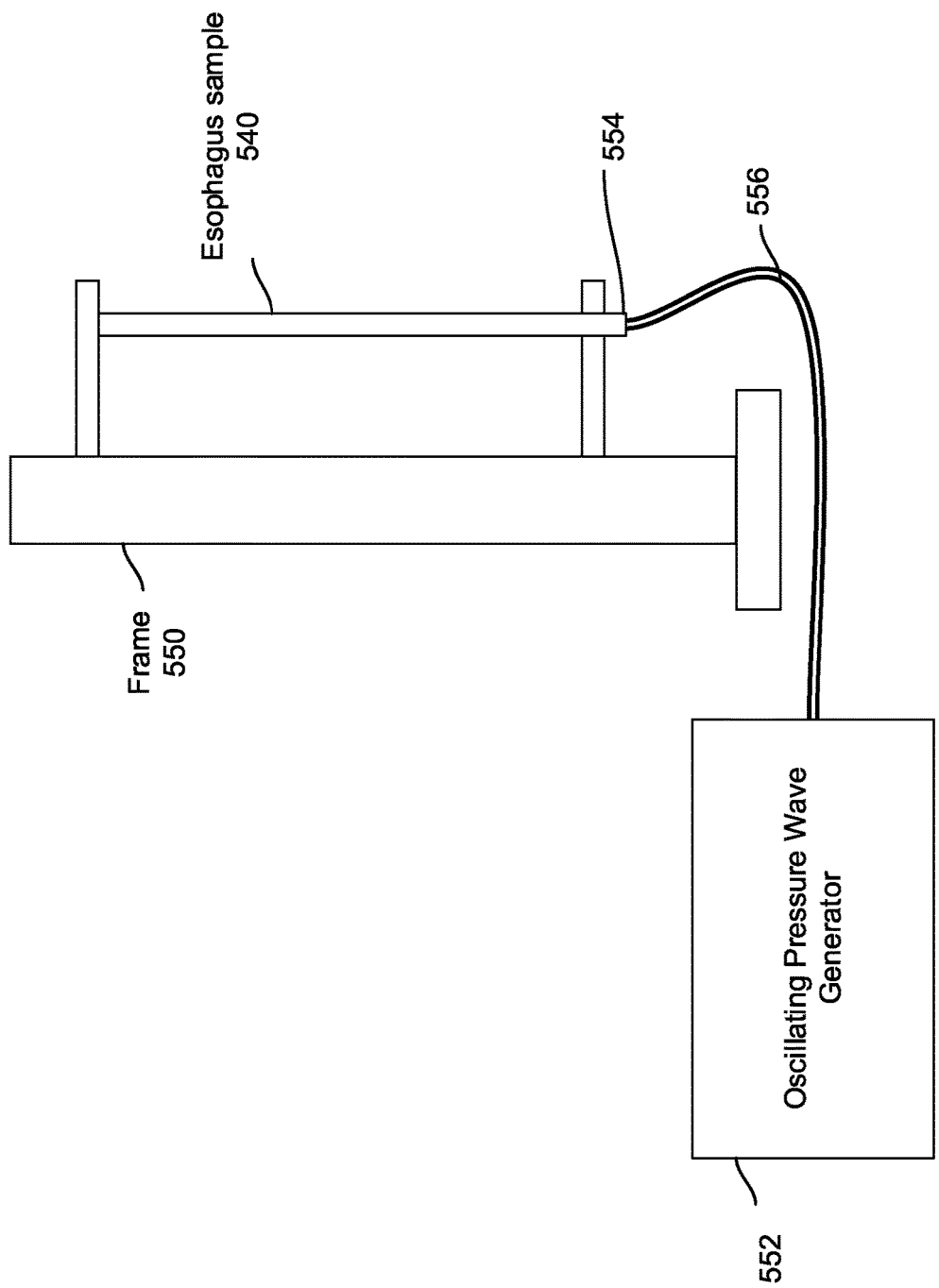
FIG. 9 is a photograph of a model for testing a temporary occlusion device for providing temporary occlusion of the esophagus including a sample of a human esophagus extracted from a human cadaver and a pump for mimicking gastric flow according to an aspect of the disclosure.

In other examples, as shown in FIG. 9, an experimental method for testing an exemplary temporary occlusion device using a sample esophagus 540 from a human cadaver is illustrated. In order to perform these tests, a portion of a trachea was dissected from a human cadaver. To overcome sphincter resistance of the esophagus sample 540, the esophagus was disconnected from the stomach by performing a complete esophagotomy. The esophagus was then fixed in a vertical position by a frame 550, as shown in FIG. 9. An oscillating pressure wave generator 552 was connected to the distal end 554 of the esophagus via small diameter silicone tubing 556. The temporary occlusion device 10 was then manually inserted into the esophagus 540 and deployed with a guidewire method.

Testing was performed by providing room temperature fluid from the pressure generator 552 to the distal end 554 of the esophagus 540 through the tubing 556. A pressure sensor (not shown) was positioned within the esophagus to measure pressure generated by the applied fluid. Baseline values for flow through the esophagus prior to insertion of the device 10 were compared to results following placement of the device 10 to determine an ability of the device 10 to occlude flow through the esophagus 540. Initial testing revealed only partial occlusion of flow with a hexagonal stent based structure and no migration of the stent device was appreciated. Tests were also performed using the tulip-shaped design (shown in FIGS. 1, 2A, and 2B) and a balloon catheter. It was determined that a frame device, such as the device 10 shown in FIGS. 1, 2A, and 2B, could withstand a pressure of about 100 mmHg before fluid leakage occurred. A balloon type device, as shown in FIG. 6, was found to withstand pressure of about 140 mmHg prior to leakage.

In other examples, the pressure generator 552 is replaced by a compressible balloon (not shown) to more closely mimic pressurized fluid leaving the stomach and entering the esophagus. For example, an elastic balloon and stopcock valve could be connected to a distal end of the esophagus sample. When the stopcock is opened, pressurized fluid is applied to the esophagus sample in which the temporary occlusion device is deployed. The esophagus sample can be observed to determine whether the deployed temporary occlusion device prevents or restricts fluid flow through the esophagus. In a similar manner, maximum pressure required to cause the temporary occlusion device to begin leaking could also be observed.

While several examples and embodiments of the esophagus temporary occlusion device and deployment methods are shown in the accompanying figures and described hereinabove in detail, other examples and embodiments will be apparent to, and readily made by, those skilled in the art without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

Preferred and non-limiting aspects or embodiments of the present invention will now be described in the following numbered clauses:

Clause 1: A temporary esophagus occlusion device for providing temporary occlusion of the esophagus during intubation of a patient, comprising: a frame configured to transition between a contracted state, in which it can be swallowed by the patient, and an expanded state, wherein in the expanded state, the frame has a maximum outer diameter sufficient to span an inner diameter of the esophagus of the patient; a flexible cover connected to and extending over at least a portion of the frame when the frame is in the expanded state to at least partially block flow of fluid and/or solid materials through the esophagus; and a guidewire attached to the frame, sized to be swallowed by the patient along with the frame and having a proximal end portion configured to remain external to the patient's body and a distal end connected to a proximal end of the frame.

Clause 2: The device of clause 1, wherein in the expanded state, an outer maximum diameter of the frame is between 2.0 cm and 4.0 cm.

Clause 3: The device of clause 1 or clause 2, wherein in the contracted state, an outer maximum diameter of the frame is less than 1.0 cm.

Clause 4: The device of any of clauses 1-3, wherein the frame comprises a plurality of elongated members comprising end portions connected to and extending at least one of radially and longitudinally outwardly from a distal end portion of the guidewire.

Clause 5: The device of clause 4, wherein the elongated members are between 0.2 mm and 0.8 mm thick.

Clause 6: The device of clause 4 or clause 5, wherein the elongated members comprise a metallic shape memory material.

Clause 7: The device of any of clauses 4-6, wherein the elongated members are bent at a middle portion thereof to form petal shaped lattices, and wherein opposing ends of the elongated members are bound together at a proximal end of the frame.

Clause 8: The device of clause 7, further comprising at least one circumferential strut extending around the lattices formed by the elongated members.

Clause 9: The device of any of clauses 4-8, wherein a proximal portion of the elongated members comprise a narrower cross section than distal portions of the elongated members.

Clause 10: The device of any of clauses 1-9, wherein the guidewire comprises a flexible metallic member of between about 0.01 mm and 0.1 mm in diameter.

Clause 11: The device of any of clauses 1-10, where the cover comprises a flexible sheet formed from at least one of polyester and Polytetrafluoroethylene (ePTFE).

Clause 12: The device of clause 11, wherein the flexible sheet is between 80 μm and 120 μm thick.

Clause 13: The device of any of clauses 1-12, further comprising a catheter tube configured to advance over the guidewire to a position adjustment to a proximal end of the frame.

Clause 14: The device of clause 13, wherein, in the collapsed state, the frame is disposed within a proximal portion of the catheter tube such that contact between the frame and an inner sidewall of the tube maintains the frame in the collapsed state.

Clause 15: A system for providing negative pressure therapy to a gastric cavity of a patient, the system comprising: the device of clause 13 or clause 14; and a suction device in fluid communication with a proximal end of a lumen defined by the catheter tube for drawing gastric fluid from the patient's stomach through the catheter tube.

Clause 16: The system of clause 15, further comprising an endotracheal tube configured for placement in the patient's trachea or lungs while the occlusion device is in the expanded state within the patient's esophagus.

Clause 17: A method for deploying a temporary occlusion device in an esophagus of a conscious patient, the method comprising: providing a temporary occlusion device, the temporary occlusion device comprising an expandable frame configured to transition between a contracted state and an expanded state, wherein in the expanded state, the frame has a diameter sufficient to span an inner diameter of the esophagus of the patient, a flexible cover connected to and extending over at least a portion of the frame when the frame is in the expanded state, to at least partially block flow of fluid and/or solid materials through the esophagus, and a guidewire attached to the frame; causing the patient to swallow the temporary occlusion device in the contracted state, such that a portion of the guidewire remains external to the patient's mouth; and deploying the expandable frame at a desired position in the patient's esophagus, thereby at least partially sealing a portion of the patient's esophagus from gastric fluid from the patient's stomach.

Clause 18: The method of clause 17, wherein the patient is awake and conscious while swallowing the temporary occlusion device.

Clause 19: The method of clause 17 or clause 18, wherein the expandable frame is deployed in the patient's esophagus about 20 cm to 40 cm from the patient's upper teeth.

Clause 20: The method of any of clauses 17-19, wherein the temporary occlusion device further comprises a catheter tube which, when the frame is in the collapsed state, at least partially encloses the frame, and wherein deploying the frame comprises one of retracting the tube from the frame to expose the frame and pushing the frame out of a distal end of the tube.

Clause 21: The method of any of clauses 17-20, wherein the frame comprises a shape memory material and wherein the frame automatically deploys when the shape memory material is exposed to an activating condition.

Clause 22: The method of clause 21, further comprising retracting the frame into the catheter tube and removing the frame and catheter tube from the patient's body through the patient's mouth.

Clause 23: The method of clause 22, further comprising exposing the shape memory material to a substance of a sufficient temperature to cause the frame to collapse to its contracted state prior to retracting the frame into the catheter tube.

Clause 24: A method for intubation of a patient with an endotracheal tube, the method comprising: providing a temporary occlusion device, the temporary occlusion device comprising an expandable frame configured to transition between a contracted state and an expanded state, wherein in the expanded state, the frame has a diameter sufficient to span an inner diameter of the esophagus of the patient, a flexible cover connected to and extending over at least a portion of the frame when the frame is in the expanded state to at least partially block flow of fluid and/or solid materials through the esophagus, and a guidewire connected to the frame; causing the patient to swallow the temporary occlusion device in the contracted state, such that a portion of the guidewire remains external to the patient's mouth; deploying the expandable frame at a desired position in the patient's esophagus; after deployment of the expandable frame of the occlusion device, inserting a distal end of an endotracheal tube through the patient's mouth and into the patient's trachea or lungs; deploying a balloon or cuff of the endotracheal tube to at least partially seal the lungs and/or trachea; and removing the temporary occlusion device from the esophagus after the endotracheal tube is deployed.

Clause 25: A method for placement of an orogastric tube in a stomach of a patient, the method comprising: providing an anchor device comprising a guidewire and a wire frame mounted to a distal end of the guidewire; causing the patient to swallow the anchor device, such that a portion of the guidewire remains external to the patient's mouth; permitting the frame and guidewire connected thereto to advance to a desired position within the patient's esophagus; and advancing the orogastric tube over the guidewire and past the frame to position a distal end of the orogastric tube in the patient's stomach.

Clause 26: The method of clause 25, wherein the anchor device further comprises a flexible cover connected to and extending over at least a portion of the frame to at least partially block flow of fluid and/or solid materials through the esophagus.

Clause 27: The method of clause 25 or clause 26, further comprising connecting a proximal portion of the orogastric tube to a suction device and, after the distal end of the orogastric tube is advanced to the patient's stomach, actuating the suction device to draw gastric fluid from the stomach.

Clause 28: The method of any of clauses 25-27, wherein the patient is awake and conscious while swallowing the anchor device.

Clause 29: The method of any of clauses 25-28, wherein the desired position within the patient's esophagus is about 20 cm to 40 cm from the patient's upper teeth.

Clause 30: The method of any of clauses 25-29, wherein the frame is configured to transition between a contracted state and an expanded state, wherein in the expanded state, the frame has a maximum outer diameter sufficient to span an inner diameter of the esophagus of the patient, and wherein the anchor device further comprises a catheter tube which, when the frame is in the collapsed state, at least partially encloses the frame.

Clause 31: The method of clause 30, further comprising deploying the frame at the desired position in the patient's esophagus by one of retracting the catheter tube from the frame to expose the frame and pushing the frame out of a distal end of the tube.

The invention claimed is:

1. A temporary esophagus occlusion device for providing temporary occlusion of the esophagus during intubation of a patient, comprising:
   a frame configured to transition between a contracted state, in which it is configured to be swallowed by the patient when the patient is conscious and awake, and an expanded state, wherein in the expanded state, the frame has a maximum outer diameter sufficient to span an inner diameter of the esophagus of the patient;
   a flexible cover connected to and extending over at least a portion of the frame when the frame is in the expanded state to at least partially block flow of fluid and/or solid materials through the esophagus; and
   an ultrathin metallic guidewire attached to the frame having an outer diameter of about 0.01 mm to about 0.1 mm, the guidewire being sized to be swallowed by the patient when the patient is conscious and awake along with the frame and having a proximal end portion configured to remain external to the patient's body and a distal end connected to a proximal end of the frame.

2. The device of claim 1, wherein in the expanded state, an outer maximum diameter of the frame is between 2.0 cm and 4.0 cm, and/or wherein in the contracted state, an outer maximum diameter of the frame is less than 1.0 cm.

3. The device of claim 1, wherein the frame comprises a plurality of elongated members comprising end portions connected to and extending at least one of radially and longitudinally outwardly from a distal end portion of the guidewire, and
   wherein the elongated members are between 0.2 mm and 0.8 mm thick, the elongated members comprise a metallic shape memory material, and/or a proximal portion of the elongated members comprise a narrower cross section than distal portions of the elongated members.

4. The device of claim 3, wherein the elongated members are bent at a middle portion thereof to form petal shaped lattices, and wherein opposing ends of the elongated members are bound together at a proximal end of the frame,
the device further comprising at least one circumferential strut extending around the lattices formed by the elongated members.

5. The device of claim 3, wherein the plurality of elongated members are connected to the guidewire by welding, soldering, or using one or more adhesives or fasteners.

6. The device of claim 1, where the cover comprises a flexible sheet formed from at least one of polyester and Polytetrafluoroethylene (ePTFE).

7. The device of claim 6, wherein the flexible sheet is between 80 μm and 120 μm thick.

8. The device of claim 1, further comprising a catheter tube configured to advance over the guidewire to a position adjacent to a proximal end of the frame.

9. The device of claim 8, wherein, in the collapsed state, the frame is disposed within a proximal portion of the catheter tube such that contact between the frame and an inner sidewall of the tube maintains the frame in the collapsed state.

10. A system for providing negative pressure therapy to a gastric cavity of a patient, the system comprising:
the device of claim 8, wherein, when the frame is in the contracted state, the device is configured to be swallowed by the patient while the patient is conscious and awake; and
a suction device in fluid communication with a proximal end of a lumen defined by the catheter tube for drawing gastric fluid from the patient's stomach through the catheter tube.

11. The system of claim 10, further comprising an endotracheal tube configured for placement in the patient's trachea or lungs while the occlusion device is in the expanded state within the patient's esophagus.

12. A method for deploying a temporary occlusion device in an esophagus of a conscious patient, the method comprising:
providing the temporary occlusion device of claim 1;
causing the patient to swallow the temporary occlusion device in the contracted state by the patient's natural swallowing mechanism, such that a portion of the guidewire remains external to the patient's mouth, wherein the patient is awake and conscious while swallowing the temporary occlusion device; and
deploying the expandable frame at a desired position in the patient's esophagus, thereby at least partially sealing a portion of the patient's esophagus from gastric fluid from the patient's stomach.

13. The method of claim 12, wherein the device is deployed about 20 cm to about 40 cm from the patient's upper teeth.

14. The device of claim 1, wherein the guidewire is about 35 cm to about 45 cm in length.

15. The device of claim 1, wherein the frame in the contracted state, the flexible cover, and a portion of the guidewire are enclosed in a dissolvable capsule sized to be swallowed by the awake and conscious patient.

16. The device of claim 1, wherein the frame in the contracted state, the flexible cover, and a portion of the guidewire are configured to be swallowed by the patient's natural swallowing mechanism.

17. The device of claim 1, wherein the frame is directly and fixedly connected to a distal end of the guidewire.

18. A method for intubation of a patient with an endotracheal tube, the method comprising:
providing a temporary occlusion device, the temporary occlusion device comprising an expandable frame configured to transition between a contracted state and an expanded state, wherein in the expanded state, the frame has a diameter sufficient to span an inner diameter of the esophagus of the patient, a flexible cover connected to and extending over at least a portion of the frame when the frame is in the expanded state to at least partially block flow of fluid and/or solid materials through the esophagus, and an ultrathin metallic guidewire connected to the frame having an outer diameter of about 0.01 mm to about 0.1 mm;
causing the patient to swallow the temporary occlusion device in the contracted state by the patient's natural swallowing mechanism while the patient is conscious and awake, such that a portion of the guidewire remains external to the patient's mouth;
deploying the expandable frame at a desired position in the patient's esophagus;
after deployment of the expandable frame of the occlusion device, inserting a distal end of an endotracheal tube through the patient's mouth and into the patient's trachea or lungs;
deploying a balloon or cuff of the endotracheal tube to at least partially seal the lungs and/or trachea; and
removing the temporary occlusion device from the esophagus after the endotracheal tube is deployed.

19. A method for placement of an orogastric tube in a stomach of a patient, the method comprising:
providing an anchor device comprising an ultrathin metallic guidewire having an outer diameter of about 0.01 mm to about 0.1 mm and a wire frame mounted to a distal end of the guidewire;
causing the patient to swallow the anchor device by the patient's natural swallowing mechanism, such that a portion of the guidewire remains external to the patient's mouth, wherein the patient is awake and conscious while swallowing the anchor device;
permitting the frame and guidewire connected thereto to advance to a desired position within the patient's esophagus, wherein the desired position is about 20 cm to 40 cm from the patient's upper teeth; and
advancing the orogastric tube over the guidewire and past the frame to position a distal end of the orogastric tube in the patient's stomach.

20. The method of claim 19, wherein the frame is configured to transition between a contracted state and an expanded state, wherein in the expanded state, the frame has a maximum outer diameter sufficient to span an inner diameter of the esophagus of the patient, and wherein the anchor device further comprises a catheter tube which, when the frame is in the collapsed state, at least partially encloses the frame,
the method further comprising deploying the frame at the desired position in the patient's esophagus by one of retracting the catheter tube from the frame to expose the frame and pushing the frame out of a distal end of the tube.

21. A method for deploying a temporary occlusion device in an esophagus of a conscious patient, the method comprising:
providing the temporary occlusion device, wherein the temporary occlusion device comprises:
a frame configured to transition between a contracted state, in which it is configured to be swallowed by the patient when the patient is conscious and awake, and an expanded state, wherein in the expanded state, the frame has a maximum outer diameter sufficient to span an inner diameter of the esophagus of the patient;

a flexible cover connected to and extending over at least a portion of the frame when the frame is in the expanded state to at least partially block flow of fluid and/or solid materials through the esophagus; and a guidewire attached to the frame, sized to be swallowed by the patient when the patient is conscious and awake along with the frame and having a proximal end portion configured to remain external to the patient's body and a distal end connected to a proximal end of the frame;

causing the patient to swallow the temporary occlusion device in the contracted state by the patient's natural swallowing mechanism, such that a portion of the guidewire remains external to the patient's mouth, wherein the patient is awake and conscious while swallowing the temporary occlusion device;

deploying the expandable frame at a desired position in the patient's esophagus, thereby at least partially sealing a portion of the patient's esophagus from gastric fluid from the patient's stomach;

advancing a catheter tube over the guidewire of the temporary occlusion device to a position adjacent to the frame; and retracting the frame into the catheter tube and removing the frame and catheter tube from the patient's body through the patient's mouth, wherein retracting the frame comprises exposing the frame to a cold liquid to cause the frame to transition from the expanded state to the contracted state.

* * * * *

UNITED STATES PATENT AND TRADEMARK OFFICE
CERTIFICATE OF CORRECTION

| | | |
|---|---|---|
| PATENT NO. | : 11,793,961 B2 | Page 1 of 1 |
| APPLICATION NO. | : 16/341123 | |
| DATED | : October 24, 2023 | |
| INVENTOR(S) | : Youngjae Chun et al. | |

It is certified that error appears in the above-identified patent and that said Letters Patent is hereby corrected as shown below:

On the Title Page

Column 1, item (71) Applicants, Line 3, delete "Education;" and insert -- Education, Pittsburgh, PA (US); --

Column 2, item (57) Abstract, Line 3, delete "in patient" and insert -- patient --

Signed and Sealed this
Twentieth Day of February, 2024

Katherine Kelly Vidal
*Director of the United States Patent and Trademark Office*